United States Patent [19]

Nelms et al.

[11] 4,040,805

[45] Aug. 9, 1977

[54] PERSONAL MONITORING DEVICE, OR DOSIMETER, FOR MEASURING EXPOSURE OF PERSONNEL TO ORGANIC VAPORS

[75] Inventors: Leonard H. Nelms; Kenneth D. Reiszner; Philip W. West, all of Baton Rouge, La.

[73] Assignee: Board of Supervisors Louisiana State University Agricultural and Mechanical College, Baton Rouge, La.

[21] Appl. No.: 735,010

[22] Filed: Oct. 22, 1976

[51] Int. Cl.² .................................................. B01D 13/00
[52] U.S. Cl. .......................................... 55/158; 55/71; 55/74; 55/387; 73/23
[58] Field of Search ............. 23/232 R, 254 R; 55/16, 55/71, 74, 158, 387; 73/23, 421.5

[56] References Cited

U.S. PATENT DOCUMENTS

| | | | |
|---|---|---|---|
| 2,557,432 | 6/1951 | Holstedt | 55/387 X |
| 3,755,800 | 8/1973 | Purt et al. | 23/254 E |
| 3,764,269 | 10/1973 | Oldham et al. | 23/254 E |
| 3,924,219 | 12/1975 | Braun | 73/23 X |
| 3,950,980 | 4/1976 | Braun et al. | 73/23 |
| 3,985,017 | 10/1976 | Goldsmith | 73/23 |

Primary Examiner—Frank A. Spear, Jr.
Assistant Examiner—Richard W. Burks
Attorney, Agent, or Firm—L. A. Proctor

[57] ABSTRACT

A personal monitoring device, dosimeter, or badge-like apparatus for measuring the exposure of personnel to pollutant toxic organic vaporous materials, notably vinyl chloride, comprised of a body portion provided with a relatively shallow top cavity, or cup-like member completely filled with an adsorbent, absorbent or reactive material, preferably activated carbon, covered, closed and physically held in place by a contiguous, thin non-porous membrane, permeable to the organic vaporous materials, notably vinyl chloride. The polluting toxic material, e.g., vinyl chloride, permeates and is transported through the membrane and is then adsorbed on the activated carbon at a rate proportional to the external concentration during the period of exposure and is subsequently removed for analysis, as by gas chromatography. The device is simple in construction, easy to use, insensitive to temperature and humidity effects, and free of other possible interferences. The device is ideally suited to personal monitoring programs required by OSHA regulations, and the analytical data obtained represents a time-weighted-average exposure which requires no further data evaluations.

10 Claims, 2 Drawing Figures

PERSONAL MONITORING DEVICE, OR DOSIMETER, FOR MEASURING EXPOSURE OF PERSONNEL TO ORGANIC VAPORS

The exposure of workers to hazardous materials, the health affects of which are not yet known, is a daily occurrence. One of the most recently discovered dangers to workers' health is the constant exposure to organic substances, particularly organic halides, and notably vinyl chloride, a material useful in the production of vinyl plastics, as a precursor in the synthesis of various organic compounds, as a refrigerant, and until recently as a propellant for aerosol sprays. The major source of atmospheric vinyl chloride pollution occurs through leakage of the vinyl chloride monomer from reaction vessels, through spillage of the monomer during handling operations, and because of the release of monomer during operations involving extrusion, molding, pressing and injection of the polymer.

It has been estimated that, in this country, nearly a half million workers in 8,000 plants producing either the monomer or polymer, inclusive of those involved in the fabrication of materials from the polymer, are subject to vinyl chloride exposure. Since the beginning of its use 35 years ago, vinyl chloride has been recognized as moderately toxic, and within 20 years of the time of its introduction it had been recognized as capable of producing chronic effects at low exposure levels causing slight change in the liver and/or kidney functions of laboratory animals. By the beginning of 1971, the possible impairment of the liver function had been observed in human workers exposed to vinyl chloride, and by 1974 the carcinogenicity of this chemical had been established. Vinyl chloride has now been established as the cause of at least 26 cases of angiosarcoma, a rare form of liver cancer, which have occurred worldwide among production workers in vinyl chloride production facilities. A high incidence of acroosteolysis of the bones of fingers, and frequent severe scaling of the skin associated with workers involved in the production of vinyl chloride plastics has been observed. Pulminary function changes, chronic cough, dizziness, increased blood pressure, fibrosis of the liver and numerous other ailments have been observed as resulting from continued, prolonged vinyl chloride exposure, and now it is believed that under certain circumstances such exposure can trigger heart attacks. Vinyl chloride exposure is now clearly recognized as extremely hazardous; a condition from which workers must be protected.

The nature of vinyl chloride pollution is such that continuous monitoring of the ambient air of the work establishment is required. Numerous, various techniques and procedures have been employed in the past to monitor vinyl chloride, but that presently recommended by the National Institute for Occupational Safety and Health, NIOSH, and that now on the market utilizes an instrument independently worn by each worker who is present, or laboring within the work establishment. Vinyl chloride is adsorbed on activated charcoal contained within a relatively long glass adsorption tube, and a battery operated pump is used to pull or draw the ambient gases through the mass of packed charcoal. The vinyl chloride is thereafter desorbed, and then analyzed by conventional gas chromatographic analysis. The vinyl chloride measure in this manner constitutes an accurate, dependable determination of the amount of vinyl chloride to which the worker was exposed during the work period. Whereas this instrument is quite accurate, and reliable, it is noisy, heavy and encumbers the freedom of movement of the worker who must wear the instrument. It is also quite complex and costly.

Recently, personal badge-like devices of various types have been developed for use in monitoring the exposure of individual industrial workers to atmospheric pollutants. For example, U.S. Pat. No. 3,924,219 which issued Dec. 12, 1975, discloses a thin wafer-like badge to be worn by persons exposed to toxic organic vapors. This device is comprised of an open top cup, providing a chamber containing a layer of a detector substance "which will adsorb, absorb, or otherwise react or entrap the gas to be measured," and the chamber is overlaid with an attenuating, or perforated sheet. A diffusion space is provided between the attenuating sheet and the detector substance which is adhered to the bottom of the cup. Related badge-like devices are also disclosed in U.S. Pat. No. 3,950,980 which issued Apr. 20, 1976. Other methods have been tried for the detection of toxic inorganic substances which are contained in gases. The techniques described involve trapping the inorganic substances in suitable absorbing solutions, after the gases have permeated through suitable polymeric membranes. These methods have met with limited success.

Despite the success of some of these methods or apparatus for use in the detection of atmospheric pollutants, there is nonetheless much yet to be desired by way of improvement, and considerably more yet required in the development of apparatus suitable for the detection and quantification of the exposure to organic pollutants, notably organic halides, and particularly vinyl chloride.

The primary objective of the present invention is, accordingly, to provide a new and improved personal badge-like monitoring device, or dosimeter, to be worn by the individual worker, suitable for the detection and quantification of exposure caused by air mixtures of vaporous organic pollutants, notably organic halide pollutants, and particularly vinyl chloride.

A specific object is to provide a device of such character which is of small size, light weight, simple construction, capable of reliable, efficient operation in the detection and quantification of vinyl chloride exposure, and which can be comfortably worn by the individual worker in a working environment.

A further object is to provide a new and improved personal monitoring device of such character which is easy to fabricate at low cost, and easy to operate in charging and recharging as required for quantification and analysis.

These and other objects are achieved in accordance with the present invention, consisting of a personal monitoring device, dosimeter, or badge-like apparatus which is comprised of a body portion provided with a relatively shallow top cavity, or cup-like member filled with a granular, or particulate sorbent material, suitably an adsorber, absorber or reactive material, preferably activated charcoal, covered, closed and physically held in place by a thin non-porous membrane permeable to organic vapor, particularly one permeable to vinyl chloride vapor. The membrane is one which has sufficiently high relative permeability to permit the transport of organic vapors through said membrane, particularly vinyl chloride vapor, which is adsorbed by the adsorber material, suitably activated charcoal, at a rate proportional to the external concentration. The vinyl chloride is adsorbed on the activated charcoal in direct proportion to the exposure of the wearer to vinyl chloride, as related to vinyl chloride concentration and time of exposure; and such time-weighted-average exposure, or quantification of the exposure, can be readily determined by chemical analysis of the charcoal by conventional techniques, particularly by gas chromatography, without further data evaluations.

The invention, and its principle of operation, will be more fully understood by reference to the following detailed description of a specific and preferred embodiment, and to the attached drawing to which reference is made in the description. In the description, similar numbers are used to designate specific parts or components. Subscripts are used to denote a plurality of identical parts, or components, and where referred to without reference to the subscripts, such designation is intended in a generic sense.

Figure 2:
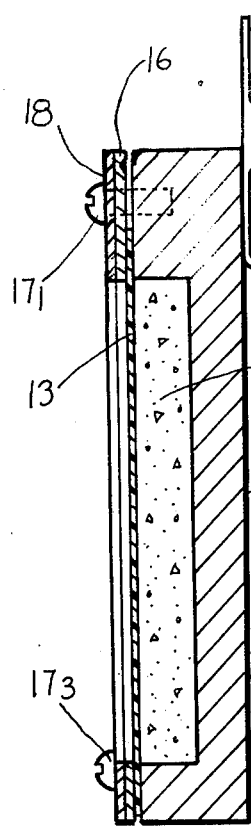
FIG. 2 is a cross-section taken through section 2—2 of the preceding figure.
Figure 1:
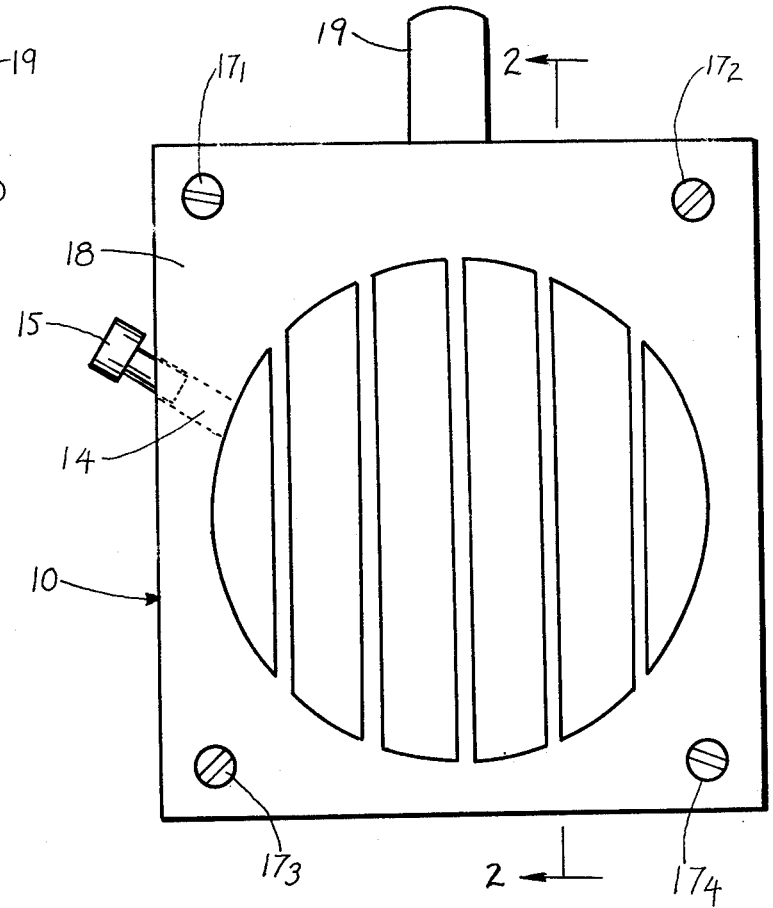
FIG. 1 depicts a tip, or plan view of a preferred type of personal monitor, particularly one found admirably suitable for the detection and quantification of vinyl chloride exposure.

Referring to the figures, there is described a badge-like device, or personal monitor 10 comprised generally of a body 11 provided with a shallow cavity providing, in effect, a shallow cup filled with an adsorber material 12, the adsorber material 12 being covered, closed and retained within the cavity of body 11 by a permeable non-porous membrane 13. A port 14 provides a means for charging fresh adsorber material 12 into the closed chamber or cavity of body 11, and a port for the withdrawal of said adsorber material 12 from the chamber for analysis to determine possible exposure, and for quantification of such exposure. A plug 15, constituted of a non-reactive or inert resilient material, is conveniently used to retain the charge of adsorber material 12 in place. Suitably, the membrane 13 is used repetitively and is cemented in place over the opening which forms the cavity within body 11, or held in place by an open centered plate 16 retained by a plurality of mounting screws $17_1$, $17_2$, $17_3$, $17_4$, or both. Suitably also, a grid plate 18, also retained in place over the membrane 13, is provided as protection for the membrane. For convenience, a clip 19 attached to the back of the body 11 via a screw 20, provides a means of attachment to the clothing of a worker, e.g., a pocket or lapel.

The body 11 of the monitor 10 can be constructed of essentially any rigid material which is essentially non-reactive with the absorber material 12, and vapors to which the monitor 10 is to be exposed. Suitably, the body 11 is constructed of metal or rigid plastics. Metals are preferred, particularly aluminum which possesses light weight and can be easily machined. Other metals which can be used are ferrous metals such as iron, iron alloys, steel, stainless steel and the like; or such metals as magnesium, brass, copper, bronze, chrome, alloys of these and other metals and the like. The plates, i.e., the appertured plate 16 and grid 18, can be similarly constructed. The rigid plastics can also be employed as suitable materials of construction. The polyfluorinated ethylene polymers, notable amount which is polytetrafluoroethylene (Teflon), are particularly outstanding. The plug 15 is suitably constructed of such plastic materials, or another material laminated or coated with such material. The screws and clip are typically constituted of metal.

Activated carbon, or charcoal, is a highly preferred adsorber material 12 for use in accordance with this invention. The material, prior to use, is dried by heating in a flow of non-reactive, or inert, gas for a time sufficient to remove the water, and suitably any other material which might interfere with the analysis of the exposed material. Suitably, for this purpose, the activated carbon, or charcoal, is heated to a temperature of from about 250° C to about 350° C for a period of about 24 hours. Exemplary of activated carbon is Darco G-60, 20-40 mesh which can be obtained from Matheson, Coleman and Bell. The depth of the chamber, or cavity within body 11 is filled with the dry activated carbon, or charcoal, providing a bed ranging in depth from about 1 to about 25 millimeters, preferably from about 2 to about 15 millimeters, and more preferably from about 2 to about 4 millimeters. The width of the chamber, or the diameter of the non-porous membrane which closes the chamber, is not critical and can vary widely, as therefore can the charge of activated charcoal. Generally, however, the total charge of activated carbon placed in the chamber, or cavity, within body 11 ranges from about 0.1 to about 2 grams, the diameter of the chamber, or cavity, ranging generally from about 20 to about 48 millimeters. Such material offers numerous advantages over other types of adsorber materials, or absorber materials or materials reactive with the vinyl chloride. The activated carbon, or charcoal, can be packed loosely into the cavity of the body 11, and hence is easily removed for analysis, as by pouring through the opening 14, and is often reusable after the analysis. There are no known interferences. Variations in temperature and humidity have no effect and there is linear response in adsorption rates over the range of 0.005 to 50 parts of vinyl chloride per million parts of total gas. Sampling periods ranging from 0.1 to 24 hours, or longer, without recharge of the monitor are entirely feasible.

Whereas activated charcoal, or carbon, is a highly preferred adsorbent, particularly for the adsorption of vinyl chloride, various other adsorbents can be used. Exemplary of such materials are silica gel, certain porous polymers such as Tenax (Applied Science Labs), Chromosorb Century Series (Johns-Manville), Porapak (Waters Associates), Carbosieve, and other materials such as activated alumina and molecular sieves.

Useful non-porous membranes are those which are non-reactive with the gaseous environment, inclusive particularly of the organic vapors which are to be adsorbed on the activated carbon, or charcoal, and which have sufficiently high permeability at from 0° C to 40° C for solution and transport of the organic vapor therethrough for adsorption on the activated carbon, or charcoal, at a rate which is proportional to the concentration of said organic vapor on the external side of the membrane. Membranes suitable for the practice of this invention are those in which the permeability does not vary significantly, preferably no more than ±20%, and more preferably no more than ±10%, over temperatures ranging from about 0° C to about 40° C, and which have an absolute permeability, Pr, to vaporous toxic organic materials within a range of from about $10 \times 10^{-9}$ to about $10,000 \times 10^{-9}$ measured by the formula:

$$PR = CC \text{ gas (RTP) cm}/sec, \text{ sq cm, cmHg P}$$

Wherein, within the numerator, the expression is a measure of the volume of gas (CC) that permeates through a measured thickness of membrane (cm) at 25° C and 1 atmosphere, and within the denominator, the expression is a measure of the rate of permeation of the gas, in seconds, over a given cross-sectional area expressed in square centimeters, at same differential pressure expressed in centimeters of mercury (Refer to Publication entitled "General Electric Permselective Membranes", GEA-8685A, 2-70 (5M) at Page 10). Illustrative of highly preferred membranes of this type are silicone-polycarbonate copolymer MEM-213 (thickness 100 cm × $10^{-4}$), dimethyl silicone, single backing (thickness 25 cm × $10^{-4}$), dimethyl silicone, unbacked (thickness 25 cm × $10^{-4}$), and dimethyl silicone, double backing (thickness 25 cm × $10^{-4}$), all of which are available from General Electric Company. Silicone rubber (thickness 100 cm × $10^{-4}$) as obtained from Union Carbide, is also a highly satisfactory membrane. The average thickness of suitable membranes generally ranges from about 0.5 to about 10 mils, preferably from about 1 to about 3 mils.

Permeation of a gas through a non-porous membrane occurs in three distinct steps, to wit: (1) gas is dissolved in the membrane; (2) the gas migrates or is transported through the membrane, and (3) the dissolved gas evaporates at the back side of the membrane and is adsorbed on the charcoal. In view of the variables involved (the principles of which have been documented by K. D. Reiszner in "Spectrophotometric Determination of Average Concentration of Sulfur Dioxide in Air by Permeation through Polymer Membranes," Ph.D. Dissertation, L.S.U. 1972), to assure accuracy it is necessary to calibrate each monitoring device, dosimeter or badge-like apparatus individually since the membranes employed are rarely, if ever, of completely uniform thickness. This is accomplished by exposing the device to a known concentration of vinyl chloride in air. Air is first dehumidified and cleaned by passage through columns of charcoal and silica gel. Clean, dry air is then passed at uniform flow rate over a permeation tube of design described by A. E. O'Keefe and G. C. Ortman, *Anal. Chem.* 38 760 (1966), the permeation tube emitting vinyl chloride at a known constant rate which provides a primary standard for the calibration procedure. The standard concentration of vinyl chloride in air is passed over the exposure chamber where the monitoring devices are exposed for calibration. Subsequent determination of the amount of vinyl chloride adsorbed on the charcoal from a given device allows the calculation of a permeation constant for each monitoring device. This constant is calculated by the following equation:

$$k = Ct/w$$

where in
$k$ = constant
$C$ = Concentration of vinyl chloride, ppm
$t$ = time of exposure, in hours
$w$ = amount of vinyl chloride adsorbed, g This constant is then used for the calculation of the average concentration of vinyl chloride in an unknown atmosphere by using the equation:

$$C = wk/t$$

where
$C$ = time-weighted-average vinyl chloride concentration, ppm

It is apparent that various changes, such as in the materials of construction, or in the absolute or relative dimension of the monitoring device, dosimeter or badge-like device itself is possible, or in the nature and thickness of the membrane, or in the weight, quantity or nature of the adsorber material, without departing the spirit and scope of the invention, as will be apparent to those skilled in this art.

Having described the invention, what is claimed is:

1. A monitoring device useful for quantitatively determining the exposure of a wearer of the device to an air mixture of a toxic vaporous organic pollutant, comprised of a body provided with a shallow top cavity filled with a particulate sorbent material covered and physically held in place by a contiguous, non-reactive, non-porous membrane, the permeability of which does not vary substantially within the range of about 0° C to about 40° C, and which has an absolute permeability to said pollutant ranging from about $10 \times 10^{-9}$ to about $10,000 \times 10^{-9}$, such that the toxic vaporous organic pollutant can be dissolved within, transported through the membrane, sorbed within the sorbent material, and which can be subsequently removed after the period of exposure for analysis to provide a timeweighted-average exposure.

2. The apparatus of claim 1 wherein the toxic vaporous organic pollutant is vinyl chloride.

3. The apparatus of claim 1 wherein the sorbent material is activated carbon, or charcoal.

4. The apparatus of claim 1 wherein the permeability variation of the membrane between the ranges 0° C to 40° C is no more than about ±20%.

5. The apparatus of claim 1 wherein the membrane ranges in average thickness from about 0.5 to about 10 mils.

6. The apparatus of claim 5 wherein the average thickness of the membrane ranges from about 1 to about 3 mils.

7. The apparatus of claim 5 wherein the membrane is a dimethyl silicone.

8. The apparatus of claim 1 wherein the membrane covering the shallow cavity is provided with an open centered cover plate, and grid plate mounted atop the cover plate.

9. The apparatus of claim 1 wherein the body of the monitoring device contains a capped opening which permits charging and discharging of the sorbent contents without removal of the membrane.

10. A monitoring device useful for the detection and and quantification of the exposure of a wearer of the device to an air-vinyl chloride mixture, which comprises: a body provided with a shallow top cavity which is filled with particulate activated carbon, covered and physically retained in place by a membrane permeable to vinyl chloride which is dissolved within, transported through, then released from the opposite side of said membrane and then adsorbed on the activated carbon in direct proportion to the exposure of the wearer to vinyl chloride as related to the external vinyl chloride concentration and time of exposure.

* * * * *